United States Patent
Shelly et al.

(10) Patent No.: US 12,011,286 B2
(45) Date of Patent: Jun. 18, 2024

(54) DETECTING UNDIAGNOSED SLEEP DISORDERED BREATHING USING DAYTIME SLEEPINESS AND NIGHTTIME OBSTRUCTIVE SLEEP APNEA (OSA) SEVERITY

(71) Applicant: KONINKLIJKE PHILIPS N.V., Eindhoven (NL)

(72) Inventors: Benjamin Irwin Shelly, Pittsburgh, PA (US); Gaurav Trivedi, Pittsburgh, PA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 488 days.

(21) Appl. No.: 17/038,019

(22) Filed: Sep. 30, 2020

(65) Prior Publication Data
US 2021/0282707 A1  Sep. 16, 2021

Related U.S. Application Data

(60) Provisional application No. 62/990,110, filed on Mar. 16, 2020.

(51) Int. Cl.
*A61B 5/00* (2006.01)
*A61B 5/0205* (2006.01)
(Continued)

(52) U.S. Cl.
CPC .......... *A61B 5/4818* (2013.01); *A61B 5/0205* (2013.01); *A61B 5/02405* (2013.01); *A61B 5/02416* (2013.01); *A61B 5/08* (2013.01); *A61B 5/1102* (2013.01); *A61B 5/1118* (2013.01); *A61B 5/316* (2021.01); *A61B 5/318* (2021.01); *A61B 5/369* (2021.01); *A61B 5/372* (2021.01); *A61B 5/383* (2021.01); *A61B 5/389* (2021.01); *A61B 5/398* (2021.01); *A61B 5/4088* (2013.01); *A61B 5/4809* (2013.01); *A61B 5/4812* (2013.01); *A61B 5/4815* (2013.01); *A61B 5/4836* (2013.01); *A61B 5/6801* (2013.01);
(Continued)

(58) Field of Classification Search
CPC ... A61B 5/4806; A61B 5/4809; A61B 5/4812; A61B 5/4815; A61B 5/4818; G16H 40/67
See application file for complete search history.

(56) References Cited

U.S. PATENT DOCUMENTS 7,130,687 B2  10/2006  Cho
7,593,767 B1 *  9/2009  Modarres ............. A61B 5/4818
                                                             600/534
(Continued)

OTHER PUBLICATIONS

International Search Report and Written Opinion, International Application No. PCT/EP2021/055829, dated Jun. 9, 2021.

*Primary Examiner* — John R Downey

(57) ABSTRACT

An apparatus and method for detecting undiagnosed sleep disordered breathing uses daytime sleepiness and nighttime Obstructive Sleep Apnea (OSA) severity. This involves detecting people with excessive daytime sleepiness (and high likelihood of falling asleep during the day) caused by OSA through objective and subjective daytime and nighttime monitoring. Screening is provided for those who are most likely to be suffering a daytime impact of their sleep apnea and thus most likely to respond positively to a potential diagnosis, and notifying these people is also provided.

6 Claims, 1 Drawing Sheet

(51) Int. Cl.

| | | |
|---|---|---|
| *A61B 5/024* | (2006.01) | |
| *A61B 5/08* | (2006.01) | |
| *A61B 5/11* | (2006.01) | |
| *A61B 5/316* | (2021.01) | |
| *A61B 5/318* | (2021.01) | |
| *A61B 5/369* | (2021.01) | |
| *A61B 5/372* | (2021.01) | |
| *A61B 5/383* | (2021.01) | |
| *A61B 5/389* | (2021.01) | |
| *A61B 5/398* | (2021.01) | |
| *G01P 13/00* | (2006.01) | |
| *G16H 10/20* | (2018.01) | |
| *G16H 20/10* | (2018.01) | |
| *G16H 20/30* | (2018.01) | |
| *G16H 40/63* | (2018.01) | |
| *G16H 40/67* | (2018.01) | |
| *G16H 50/20* | (2018.01) | |
| *G16H 50/30* | (2018.01) | |
| *G16H 50/70* | (2018.01) | |
| *A61B 5/1455* | (2006.01) | |
| *A61B 5/378* | (2021.01) | |
| *A61B 5/38* | (2021.01) | |
| *G09B 19/00* | (2006.01) | |

(52) U.S. Cl.
CPC .......... *A61B 5/6892* (2013.01); *A61B 5/6898* (2013.01); *A61B 5/7246* (2013.01); *A61B 5/7264* (2013.01); *A61B 5/7267* (2013.01); *A61B 5/7278* (2013.01); *G01P 13/00* (2013.01); *G16H 10/20* (2018.01); *G16H 20/10* (2018.01); *G16H 20/30* (2018.01); *G16H 40/63* (2018.01); *G16H 40/67* (2018.01); *G16H 50/20* (2018.01); *G16H 50/30* (2018.01); *G16H 50/70* (2018.01); *A61B 5/024* (2013.01); *A61B 5/02438* (2013.01); *A61B 5/0816* (2013.01); *A61B 5/1103* (2013.01); *A61B 5/1123* (2013.01); *A61B 5/14552* (2013.01); *A61B 5/378* (2021.01); *A61B 5/38* (2021.01); *A61B 5/6802* (2013.01); *A61B 5/6891* (2013.01); *G09B 19/00* (2013.01)

(56) References Cited

U.S. PATENT DOCUMENTS

| | | | |
|---|---|---|---|
| 2005/0061315 | A1 | 3/2005 | Lee |
| 2008/0146893 | A1* | 6/2008 | Levendowski ...... A61B 5/0002 600/300 |
| 2010/0100004 | A1* | 4/2010 | van Someren ......... G16H 50/30 600/595 |
| 2012/0212345 | A1* | 8/2012 | Harman ................ A61B 7/003 340/575 |
| 2015/0073289 | A1 | 3/2015 | Lim |
| 2016/0045161 | A1* | 2/2016 | Alshaer ................ A61B 5/097 600/538 |
| 2016/0296165 | A1* | 10/2016 | Moore ................ A61B 5/7282 |
| 2017/0071533 | A1* | 3/2017 | Warren ............... A61B 5/7275 |
| 2017/0196760 | A1* | 7/2017 | Hyde ................ A61M 16/0069 |
| 2018/0028111 | A1* | 2/2018 | Waris ..................... A61B 5/165 |
| 2018/0028772 | A1* | 2/2018 | Davis .................. A61M 16/06 |
| 2020/0289321 | A1* | 9/2020 | Luo ..................... A61B 5/4812 |
| 2020/0359954 | A1* | 11/2020 | Sunagawa ............... G06F 21/32 |

* cited by examiner

DETECTING UNDIAGNOSED SLEEP DISORDERED BREATHING USING DAYTIME SLEEPINESS AND NIGHTTIME OBSTRUCTIVE SLEEP APNEA (OSA) SEVERITY

CROSS-REFERENCE TO PRIOR APPLICATION

This application claims the benefit of U.S. Provisional Patent Application No. 62/990,110, filed Mar. 16, 2020 which is incorporated by reference herein.

BACKGROUND OF THE INVENTION

1. Field of the Invention

The present invention pertains to the potential need for a sleep disordered breathing treatment program, and, in particular, to an apparatus and a method for using daytime sleepiness and nighttime Obstructive Sleep Apnea (OSA) severity in the detecting of undiagnosed sleep disordered breathing and informing a patient.

2. Description of the Related Art

Numerous types of sleep disordered breathing disorders, such as obstructive sleep apnea (OSA) and other such disorders, are known to exist. Likewise, numerous different types of therapy treatments are provided in order to treat such sleep disordered breathing disorders.

Over 80% of the estimated 22 million Americans suffering from moderate and severe sleep apnea remain undiagnosed: https://www.sleepapnea.org/learn/sleep-apnea-information-clinicians/. Untreated OSA can lead to chronic diseases like type 2 diabetes, high blood pressure, chronic heart failure, atrial fibrillation, stroke, and other cardiovascular problems. Furthermore, untreated OSA is a factor in many traffic accidents and accidents with heavy machinery, and this is often due to excessive daytime sleepiness observed by many patients before the disease is recognized.

While OSA is drastically under-diagnosed, only approximately 40% of those with OSA suffer from Excessive Daytime Sleepiness (EDS). While the remaining 60% may also benefit from treatment of OSA, they nevertheless may not be particularly happy to be notified that they have a latent sleep disorder, as opposed to those 40% who suffer from EDS. That is, many people may not necessarily wish to be diagnosed with OSA, especially those who have no noted daytime impact from their sleep-disordered breathing. Additionally, for mild OSA (i.e. $5<=RDI<=15$ events/hr, expression of excessive daytime sleepiness is one of the potential required symptoms for an OSA diagnosis (i.e. someone without symptoms and a mild RDI will not be diagnosed with OSA). Thus, excessive daytime sleepiness might be a necessary signal for those with "mild" OSA. The third edition of the International Classification of Sleep Disorders (ICSD-3) defines OSA as a PSG-determined obstructive respiratory disturbance index (RDI)≥5 events/hr associated with the typical symptoms of OSA (e.g., unrefreshing sleep, daytime sleepiness, fatigue or insomnia, awakening with a gasping or choking sensation, loud snoring, or witnessed apneas), or an obstructive RDI≥15 events/hr (even in the absence of symptoms). https://jcsm.aasm.org/doi/10.5664/jcsm.6506.

Improvements in the way in which treatment is offered to patients suffering from sleep disordered breathing disorders thus would be desirable.

SUMMARY OF THE INVENTION

Accordingly, it is an object of the present invention to provide an improved apparatus and method for detecting undiagnosed sleep disordered breathing using daytime sleepiness and nighttime OSA severity that overcomes the shortcomings of conventional systems and methods for detecting undiagnosed sleep disordered breathing. This object is achieved according to one embodiment of the present invention by detecting people with excessive daytime sleepiness (and high likelihood of falling asleep during the day) caused by OSA through objective and subjective daytime and nighttime monitoring. Using the disclosed and claimed concept, screening is provided for those who are most likely to be suffering a daytime impact of their sleep apnea and thus most likely to respond positively to a potential diagnosis, and notifying these people is also provided.

Accordingly, aspects of the disclosed and claimed concept are provided by an improved method of informing a person of a possible need for sleep disordered breathing therapy, the general nature of which can be stated as including, with the use of an electronic device that is at least one of situated on the person and carried by the person, detecting that the person experiences Excessive Daytime Sleepiness (EDS), with the use of at least one of the electronic device and another electronic device, determining that the person may have a Sleep Disordered Breathing Disorder (SDBD), and based at least in part upon the detecting and the determining, outputting a notification that informs the person that they may have a need for sleep disordered breathing therapy due to the SDBD.

Other aspects of the disclosed and claimed concept are provided by an improved apparatus structured to inform a person of a possible need for sleep disordered breathing therapy, the general nature of which can be stated as including a processor apparatus, the general nature of which can be stated as including a processor and a storage, an input apparatus structured to provide input signals to the processor apparatus, an output apparatus structured to receive output signals from the processor apparatus, and the storage having stored therein a number of instructions (20) which, when executed on the processor, cause the apparatus to perform a number of operations, the general nature of which can be stated as including with the use of an electronic device that is at least one of situated on the person and carried by the person, detecting that the person experiences Excessive Daytime Sleepiness (EDS), with the use of at least one of the electronic device and another electronic device, determining that the person may have a Sleep Disordered Breathing Disorder (SDBD), and based at least in part upon the detecting and the determining, outputting a notification that informs the person that they may have a need for sleep disordered breathing therapy due to the SDBD.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the

DETAILED DESCRIPTION OF EXEMPLARY EMBODIMENTS

Figure 1:
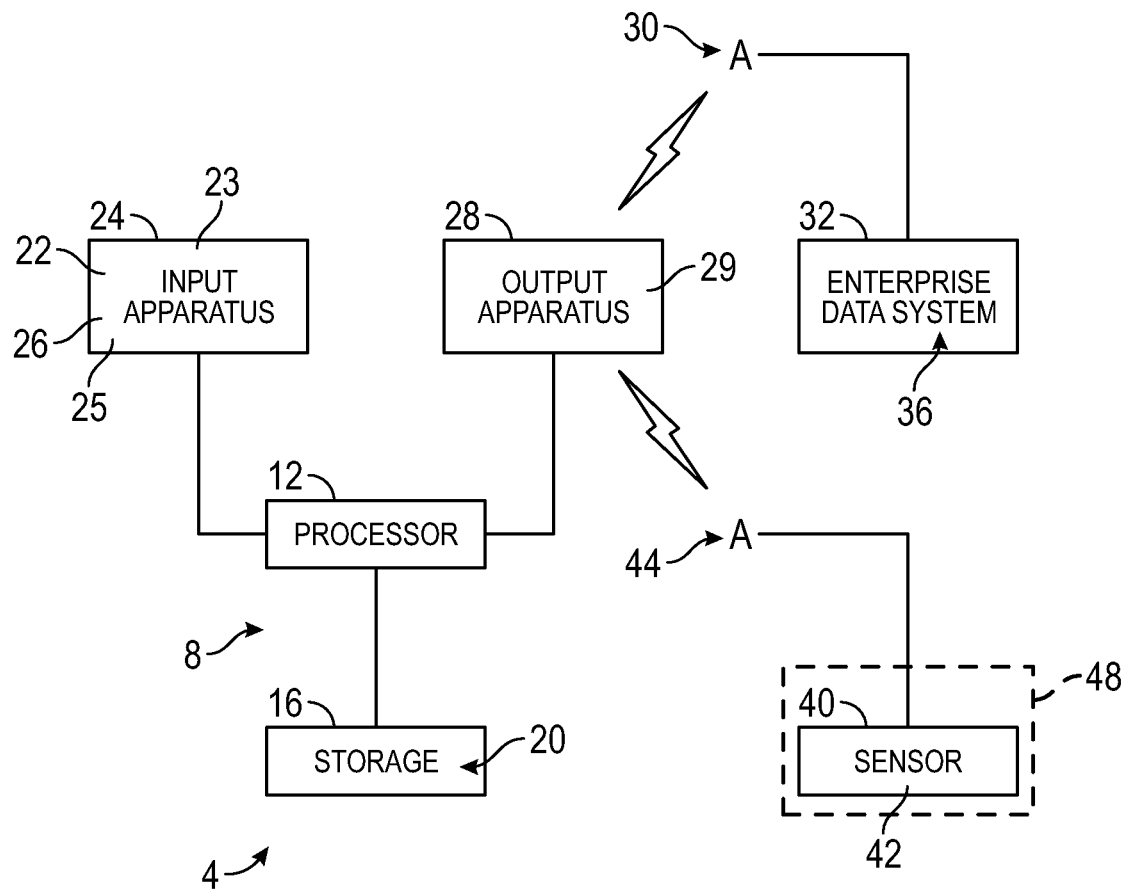
FIG. 1 is a schematic depiction of an improved apparatus in accordance with an embodiment of the disclosed and claimed concept.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Much of the population who has undiagnosed OSA does not necessarily wish to be diagnosed as having OSA. To be successful in delighting customers in a consumer space, finding the consumers who are most likely to be pleased to be alerted to a treatable sleep condition is desirable.

Known wrist wearables such as smart watches, activity monitors, and the like, can detect nighttime apnea and apnea-like events using sensors such as PhotoPlethysmoGram (PPG) sensors, reflectance pulse oximetry (SpO2) sensors, and other sensors. However, such systems currently have reduced sensitivity and specificity. Also, users who do not perceive the impact of a sleep disordered breathing disorder (SDBD) on their daily life, such as if the users are not also suffering from Excessive Daytime Sleepiness (EDS) due to the SDBD, are unlikely to seek treatment in response to a notification. Rather, such persons are likely to consider as a nuisance a notification that seeks to suggest to the person that they seek sleep disordered breathing therapy. Described herein are an advantageous apparatus 4 and method 100 for assessing sleep problems affecting patients by combining daytime and nighttime monitoring.

Apparatus 4 advantageously detects daytime drowsiness or sleepiness, such as while in a vehicle or while operating heavy machinery. Opportunities for such detection include eye blink rate detection, EEG monitoring, etc. In accordance with the disclosed and claimed concept, excessive daytime sleepiness (EDS) is measured by the prevalence of episodes of "nodding off" at non-preferred times. For instance, this can be noted with the use of a PPG by slowing of heart rate (HR) and increase of parasympathetic activation, followed immediately by abrupt movement and increases in HR and sympathetic activation.

The context of these moments of daytime sleepiness (e.g. while driving, during meetings, etc.) can also be taken into account to stratify risk and/or impact of daytime sleepiness. Additionally, times spent napping can be detected automatically and taken into account by apparatus 4 as a measure of daytime sleepiness. Thus, someone with a high level of daytime sleepiness is determined by objective data. This objective daytime sleepiness can also be confirmed by asking users questions (e.g. "Can you rate your energy level this afternoon?") or a questionnaire (e.g. Epworth Sleepiness Scale).

Thus, by combining nighttime data from apparatus 4, which can be in the form of a wearable device or other sleep tracking devices, the sensitivity of OSA screening methods is increased to advantageously identify subjects with a high likelihood of OSA and high probability of being receptive to OSA diagnosis. It is therefore possible to provide actionable alerts to populations with untreated OSA. Moreover, someone who fits the persona of having a high risk of acute accident (e.g. a car crash or an accident during use of heavy equipment) is more likely to be receptive to being notified of their sleep issues and referred for follow up therapy.

Figure 2:
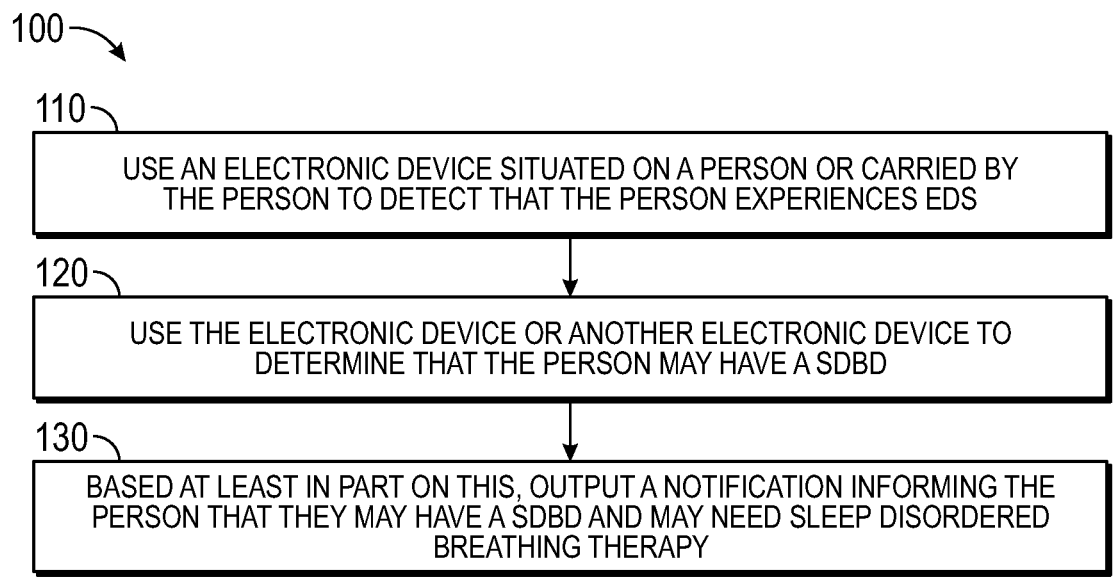
FIG. 2 is a flowchart depicting certain aspects of an improved method in accordance with an embodiment of the disclosed and claimed concept.

An improved apparatus 4 in accordance with the disclosed and claimed concept is depicted in a schematic fashion in FIG. 1. Apparatus 4 can be advantageously employed to perform and implement an improved method 100 that is also in accordance with the disclosed and claimed concept, a flowchart of which is depicted generally in FIG. 2.

Apparatus 4 can be characterized as including a processor apparatus 8 that can be said to include a processor 12 and a storage 16 that are connected with one another. Storage 16 has stored therein a number of routines 20 that are in the form of a non-transitory storage medium and that include instructions which, when executed on processor 12, cause apparatus 4 to perform certain operations such as are mentioned elsewhere herein.

Apparatus 4 can be said to further include an input apparatus 24 that provides input signals to processor 12 and an output apparatus 28 that receives output signals from processor 12. Input apparatus 24 can be said to include any of a variety of input components, and output apparatus 28 can likewise be said to include any of a variety of output components. For instance, since apparatus 4 includes a touchscreen, output apparatus 28 might be said to include a visual display 29 component of the touchscreen, and input apparatus 24 might be said to include a touch-sensitive overlay 22 component of the touchscreen that is situated atop the visual display 29. Likewise, if apparatus 4 includes a wireless transceiver, input apparatus 24 might be said to include a receiver component of the wireless transceiver, and output apparatus 28 might be said to include a transmitter component of the wireless transceiver.

Input apparatus 24 can further be said to include a PhotoPlethysmoGram (PPG) sensor 23, a reflectance pulse oximetry (SpO2) sensor 25, and an actigraphy sensor 26. In such a configuration, the apparatus 4 can be said to be in the form of a single device that includes these aforementioned sensors 23, 25, and 26 and which is in the form of a wearable device, such as a smart watch or the like. In other embodiments that are in accordance with the disclosed and claimed concept, however, the apparatus 4 might include fewer than all of the sensors 23, 25, and 26. In still other embodiments that are likewise in accordance with the disclosed and claimed concept, the apparatus 4 might take other forms, such as the form of a cellular telephone or other device that can be carried by a user.

Apparatus 4 is depicted in FIG. 1 as being in wireless communication via a first wireless link 30 with an enterprise data system 32 that itself includes a number of routines 36 that are executable on a processor of enterprise data system 32 in order to cause enterprise data system 32 to perform certain operations. Apparatus 4 is further depicted in FIG. 1 as being wirelessly in communication with another electronic device 40 via a second wireless link 44. It thus can be understood that FIG. 1 is intended to schematically depict a data processing, sensing, and support system that includes any one or more of a wide variety of components that communicate with other components in order to achieve the goals that are noted herein. As such, it is expressly pointed out that numerous different types of devices can be in communication with other devices in order to perform the operations that are mentioned herein and that meet the goals that are described herein.

In one exemplary embodiment, the routines 20 that monitor daytime sleepiness and nighttime OSA risk factors are all captured in a single wearable device, which contains the PPG 23, the reflectance SpO2 sensor 25, and the actigraphy sensor 26. Daytime sleepiness is determined by counting episodes of inadvertent sleep, and nighttime OSA risk is determined using the PPG to correlate respiratory effort along with dips in SpO2 and/or arousals from sleep. All of this detection occurs directly on apparatus 4, it being noted that some or all of the processing of the detection signals from the sensors 23, 25, and 26 can occur on the processor 12, although certain of the processing can be offloaded to the enterprise data system 32 for processing thereon depending upon the needs of the particular application.

In another exemplary embodiment, sleep tracking is done separately from daytime monitoring. More specifically, sleep tracking is performed with an under-mattress piezoelectric sensor that gathers heart rate data, respiratory data, and movement data of the patient. Daytime sleepiness is tracked using a wearable PPG sensor. As such, in this embodiment the another electronic device 40 would include a sensor 42 that serves as the piezoelectric sensor. As can be understood from FIG. 1, the piezoelectric sensor 40 is depicted as being in a situation 48 which, in this particular context, is a situation 48 situated underneath a mattress. This is particularly useful if apparatus 4 includes only the PPG 23 but fails to include the reflectance SpO2 sensor 25 and the actigraphy sensor 26. For instance, the another device 40 could be a cellular telephone that has a wireless or a wired connection with the piezoelectric sensor 42 that is situated underneath the mattress according to its situation 48.

In another exemplary embodiment, daytime sleepiness tracking is performed with an earbud-based PPG sensor, monitoring for head-nodding/jerking, as known by one skilled in the art. In such an embodiment, the sensor 42 would be the earbud-based PPG sensor, and the situation 48 could be in a position situated on the outer ear of the user. The another electronic device 40 could be in the form of a cellular telephone that has either a wired or a wireless connection with the earbud-based PPG sensor 42.

In another exemplary embodiment, daytime sleepiness tracking is performed by measuring eye blink rate during cell phone usage. In such a situation, the sensor 42 might be a camera of a cellular telephone, with a cellular telephone being the another electronic device 40. By way of example, the situation 48 in such an embodiment would be position alongside the head of the user with the camera 42 being situated such that it can detect eye blink rate of the user.

The severity of the daytime sleepiness and the severity of the detected OSA are combined in order to determine the projected receptivity of the user to OSA diagnosis information. For example, apparatus 4 may determine one or more of (or each of) an EDS severity level, an SDBD severity level, and an SDBD probability value of the uses. A high level of OSA severity along with a high probability of OSA may only need a small level of daytime sleepiness in order to generate and output a notification alert the user to the possible need for a breathing treatment program. Similarly, a user with a high detected daytime sleepiness level and medium probability and medium severity of OSA symptoms may also be alerted with such a notification.

The user is notified through a mobile application or through the routines 20 which will determine and provide to the user a severity indicator, which may include a stratified daytime sleepiness score, a nighttime sleep disturbance score, and other information in addition to or alternative thereto. The daytime sleepiness score and the nighttime sleep disturbance scores can be compared to population values and stratified based on age, gender, etc., as desired. An exemplary message that is provided as part of the notification may be as follows:

"We've noticed that you seem to be sleepy during the day. We use objective data from your watch to help monitor how well you perform during the day and how well you sleep at night. As you can note, your sleepiness level during the afternoon is in the upper 10th percentile for your age and gender. We've also noted that your sleep quality has been suffering. As you can see, you have some of the symptoms of Obstructive Sleep Apnea, including repeated interruptions in breathing and drops in your blood oxygen concentration, which you may not notice while you are sleeping. Your sleep score shows you in the upper 20th percentile for predicted OSA severity. The good news is that there is help available— seeking treatment for OSA can help with your daytime energy levels, help you feel more rested when you wake up, and has been shown to significantly improve your overall health. Let's start that journey together!"

As expected, messaging and statistics provided to the user can be refined to specific users and time periods. For example, specific times of inadvertent nodding off, such as which are detected with high probability, can be noted, as can specific statistics related to sleep quality (e.g. number, duration, and/or hourly indices of apneas, oxygen desaturations, etc.).

Alternatively or in addition, the user is notified via emailed reports that can be forwarded to a physician or employer. It is noted that any device that uses and reports daytime monitoring of sleepiness as a part of an OSA diagnostic alert could be detected as using the invention.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of determining a need for sleep disordered breathing therapy for a person, comprising:

with the use of a single wearable electronic device including a PhotoPlethysmoGram (PPG) sensor, a reflectance pulse oximetry (SpO2) sensor, and an actigraphy sensor, determining that the person experiences Excessive Daytime Sleepiness (EDS) by detecting nodding off at non-preferred times by detecting slowing of heart rate and an increase of parasympathetic activation using the PPG sensor followed immediately by detecting abrupt movement using the actigraphy sensor and by detecting an increase in heart rate and an increase of parasympathetic activation using the PPG sensor, and determining that the person experiences Sleep Disordered Breathing Disorder (SDBD) by using a PPG measurement from the PPG sensor to correlate respiratory effort with dips in SpO2 as measured by the SpO2 sensor and arousals from sleep as measured by the actigraphy sensor;

determining a daytime sleepiness score, a nighttime sleep disturbance score, and a severity indicator based at least in part upon the daytime sleepiness score and the nighttime sleep disturbance score including comparing the daytime sleepiness score and the nighttime sleep disturbance score to population values and a stratifying the daytime sleepiness score and the nighttime sleep disturbance score based on age and gender; and based at least in part upon the severity indicator, outputting a notification that informs the person that they have a need for sleep disordered breathing therapy due to the SDBD, the notification comprising the severity indicator.

2. The method of claim 1, further comprising: determining at least one of an EDS severity level, an SDBD severity level, and an SDBD probability value; and outputting the notification based at least in part upon the at least one of the EDS severity level, the SDBD severity level, and the SDBD probability value.

3. The method of claim 2 wherein the determining of the at least one of the EDS severity level, the SDBD severity level, and the SDBD probability value comprises determining each of the EDS severity level, the SDBD severity level, and an SDBD probability value, and wherein the outputting of the notification based at least in part upon the at least one of the EDS severity level, the SDBD severity level, and the SDBD probability value comprises outputting the notification based at least in part upon at least two of the EDS severity level, the SDBD severity level, and the SDBD probability value.

4. An apparatus structured to inform a person of a possible need for sleep disordered breathing therapy, comprising:

a processor apparatus comprising a processor and a storage;

an input apparatus structured to provide input signals to the processor apparatus;

an output apparatus structured to receive output signals from the processor apparatus; and the storage having stored therein a number of instructions which, when executed on the processor, cause the apparatus to perform a number of operations comprising:

with the use of a single wearable electronic device including a PhotoPlethysmoGram (PPG) sensor, a reflectance pulse oximetry (SpO2) sensor, and an actigraphy sensor, detecting that the person experiences Excessive Daytime Sleepiness (EDS) by detecting nodding off at non-preferred times by detecting slowing of heart rate and an increase of parasympathetic activation using the PPG sensor followed immediately by detecting abrupt movement using the actigraphy sensor and by detecting an increase in heart rate and an increase of parasympathetic activation using the PPG sensor, and determining that the person experiences Sleep Disordered Breathing Disorder (SDBD) by using a PPG measurement from the PPG sensor to correlate respiratory effort with dips in SpO2 as measured by the SpO2 sensor and arousals from sleep as measured by the actigraphy sensor;

determining a daytime sleepiness score, a nighttime sleep disturbance score, and a severity indicator based at least in part upon the daytime sleepiness score and the nighttime sleep disturbance score including comparing the daytime sleepiness score and the nighttime sleep disturbance score to population values and stratifying the daytime sleepiness score and the nighttime sleep disturbance score based on age and gender; and based at least in part upon the severity indicator, outputting a notification that informs the person that they have a need for sleep disordered breathing therapy due to the SDBD, the notification comprising the severity indicator.

5. The apparatus of claim 4, wherein the operations further comprise: determining at least one of an EDS severity level, an SDBD severity level, and an SDBD probability value; and outputting the notification based at least in part upon the at least one of the EDS severity level, the SDBD severity level, and the SDBD probability value.

6. The apparatus of claim 5 wherein the determining of the at least one of the EDS severity level, the SDBD severity level, and the SDBD probability value comprises determining each of the EDS severity level, the SDBD severity level, and an SDBD probability value, and wherein the outputting of the notification based at least in part upon the at least one of the EDS severity level, the SDBD severity level, and the SDBD probability value comprises outputting the notification based at least in part upon at least two of the EDS severity level, the SDBD severity level, and the SDBD probability value.

* * * * *